US00PP16552P2

(12) United States Plant Patent
Olesen

(10) Patent No.: US PP16,552 P2
(45) Date of Patent: May 16, 2006

(54) FLORIBUNDA ROSE PLANT NAMED 'POULFL003'

(50) Latin Name: *Rosa* hybrid
Varietal Denomination: Poulfl003

(75) Inventor: Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 73 days.

(21) Appl. No.: 11/002,753

(22) Filed: Dec. 1, 2004

(51) Int. Cl.
*A01H 5/00* (2006.01)

(52) U.S. Cl. ..... Plt./141
(58) Field of Classification Search ..... Plt./141, Plt./143, 145, 146, 147, 132
See application file for complete search history.

*Primary Examiner*—Anne Marie Grunberg
*Assistant Examiner*—June Hwu

(57) ABSTRACT

A new garden rose plant of the floribunda rose class which has abundant, apricot flowers and attractive foliage. This new and distinct variety has shown to be uniform and stable in the resulting generations from asexual propagation.

2 Drawing Sheets

Botanical Classification: *Rosa* hybrid.
Variety Denomination: 'Poulfl003'.

SUMMARY OF THE INVENTION

The present invention constitutes a new and distinct variety of garden rose plant, of the floribunda rose class, that originated from a controlled crossing between the female seed parent 'Poulsiana', described and illustrated in U.S. Plant Pat. No. 11,638 issued Nov. 21, 2000, and the male pollen parent, an unnamed seedling.

The two parents were crossed during the summer of 1997, and the resulting seeds were planted in a controlled environment in Fredensborg, Denmark. The new variety is named 'Poulfl003'.

The new variety may be distinguished from its female seed parent. 'Poulsiana' by the following combination of characteristics:

1. 'Poulsiana' has a more compact growth habit than 'Poulfl003'.
2. 'Poulsiana' has a petal count of 15 to 20, while 'Poulfl003' has 55 to 60 petals.
3. 'Poulsiana' has a bright yellow flower color, while flower of 'Poulfl003' are apricot.

The new variety may be distinguished from the male pollen parent, by the following combination of characteristics:

1. The pollen parent has orange flowers. 'Poulfl003' has apricot flowers.
2. The pollen parent has more flower petals than 'Poulfl003'.
3. Flowers of the pollen parent are larger in diameter than those of 'Poulfl003'.

The objective of the hybridization of this rose variety was to create a new and distinct variety for garden use with unique qualities, such as:

1. Uniform and abundant apricot flowers;
2. Vigorous, but compact growth when propagated both as a budded rose and on its own roots;
3. Disease resistance;
4. Dark green attractive foliage.

This combination of qualities is not present in previously available commercial cultivars of this type, known to the inventors, and distinguish 'Poulfl003' from all other varieties of which we are aware.

As part of the rose development program, Mogens N. Olesen germinated the seeds from the aforementioned hybridization during winter of 1997 and conducted evaluations on the resulting seedlings in a controlled environment in Fredensborg, Denmark.

'Poulfl003' was selected in the spring of 1998 by the inventors as a single plant from the progeny of the aforementioned hybridization.

Asexual reproduction of 'Poulfl003' by traditional budding and rooted cuttings was first done by Mogens N. Olesen in the nursery in Fredensborg, Denmark in July, 1998. This initial and other subsequent asexual propagations conducted in controlled environments have demonstrated that the characteristics of 'Poulfl003' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulfl003'. Specifically illustrated in the drawings:

FIG. 1.1; Side view of bud and partially opened flower, showing sepals and pedicel;

FIG. 1.2; Open flowers;

FIG. 1.3; Petals detached;

FIG. 1.4 Sepals detached, and sepals attached to receptacle, showing reproductive flower parts;

FIG. 2.1; Juvenile leaves;

FIG. 2.2; Juvenile stem exhibiting thorns;

FIG. 2.3; Mature leaves;

FIG. 2.4; Mature stem exhibiting thorns.

DETAILED DESCRIPTION OF THE VARIETY

The following is a description of 'Poulfl003', as observed in its growth in a field nursery in Jackson County, Oreg.

Observed plants are 2 years of age, and were grown on *Rosa multiflora* understock. Color references are made using The Royal Horticultural Society (London, England) Colour Chart, 1995, except where common terms of color are used.

For a comparison, several physical characteristics of the rose variety 'Poululv', a rose variety from the same inventors described and illustrated in U.S. Plant Pat. No. 15,183 dated Sep. 28, 2004, are compared to 'Poulfl003' in Chart 1.

CHART 1

| | 'Poulf1003' | 'Poululv' |
|---|---|---|
| General tonality | Yellow-Orange Group 18A with intonations of Orange Group 24B and 24C toward the center. | Yellow-Orange Group 18A to 18B with intonations of Orange-Red Group 33C to 33D. |
| Petal size. | 35 mm (l) × 35 mm (w). | 25 mm (l) × 20 (w). |
| Mature foliage color | Yellow-Green 147A | Yellow-Green 146A |

FLOWER AND FLOWER BUD

Blooming habit: Continuous.

Flower bud:

*Size.*—Upon opening, 18 to 20 mm in length from base of receptacle to end of bud. Bud diameter is normally 12 to 14 mm.

*Bud form.*—Pointed ovoid.

*Bud color.*—As the sepals unfold, the underlying tonality of flower petals is Orange Group 24D with overlying intonations of Yellow Group 12C and Greyed-Red Group 181C.

*Sepal inner surface.*—Color: Yellow-Green Group 147B and 147C. Surface: Strongly pubescent.

*Sepal outer surface.*—Color: Yellow-Green Group 146B and Yellow-Green Group 144C. Texture: Lightly pubescent.

*Sepal shape.*—Apex: Cirrhose. Base: Flat at union with receptacle. Generally subulate with a broad base

*Sepal margin.*—Margins have medium to weak foliaceous appendages on three of the five sepals.

*Sepal size.*—Normally 20 mm (l) by 9 mm (w).

*Receptacle.*—Texture: Very glabrous. Shape: Funnel shaped. Size: Normally 10 mm (l)×9 mm (w). Color: Yellow-Green Group 144B. Light anthocyanic pigments the color of Greyed-Red Group 180A observed.

*Pedicel.*—Surface: Rough. Length: 20 mm. Diameter: 3 mm. Color: Yellow-Green Group 152D to Yellow-Green Group 144C. Anthocyanic pigments Greyed-Red 180A. Strength: Strong and erect.

Flower bud development: Flower buds are borne typically in clusters of 7 flower buds per flowering stem. Inflorescence type is a corymb.

Flower bloom:

*Fragrance.*—Somewhat fruity with pungent overtones.

*Duration.*—The blooms have a duration on the plant of approximately 10 days. Petals fall cleanly away from plant after flowers have fully matured.

*Size.*—When flower are fully open, diameter is 70 to 75 mm. Depth is normally 32 mm.

*Flower shape.*—Flowers retain a tight center upon opening. As flowers mature they become an open cup with overlapping petals.

*Shape of flower, side view.*—Upon opening, Upper portion: Flat. Lower portion: Flat. After opening, Upper portion: Flattened convex. Lower portion: Concave.

*Petalage.*—Under normal conditions, flowers have 55 to 60 petals total, 23 of which are petaloids.

*Petal color.*—Upon opening, outer petals Upper surface: General intonations of Yellow Group 8C with light intonations of Greyed-Orange Group 167D to Orange Group 26C at middle zone. Lower surface: General intonations of Yellow Group 8B with light intonations of Yellow-Orange Group 23D and Orange Group 24D. Upon opening, inner petals: Upper surface: General intonations of Yellow Group 8C with light intonations of Greyed-Orange Group 167D to Orange Group 26C at middle zone. Lower surface: General intonations of Yellow Group 8B with light intonations of Yellow-Orange Group 23D and Orange Group 24D. Basal petal spots, upon opening: Upper surface: Yellow Group 6A. Lower surface: Yellow Group 8A. After opening, outer petals Upper surface: Petals have a basic color of Yellow Group 8B. Margins are Yellow-Orange Group 19C. At the middle zone, there are strong intonations of Yellow-Orange Group 22C to Greyed-Orange Group 168D. Lower surface: Petals have a basic color of Yellow Group 8B to 8C. Margins are Yellow Orange Group 19C. A weak overlay of Yellow-Orange Group 22C to Greyed-Orange Group 168D observed. After opening, inner petals: Upper surface: Petals have a basic color of Yellow Group 8B to 8C. An overlay of Orange Group 24D to Greyed-Orange Group 168D observed at middle and marginal zone. Light streaks of Yellow Group 8C observed. Lower surface: Petals have a basic color of Yellow Group 8C. Marginal zone has intonations of Orange-Red Group 31D. Basal petals spots, after opening: Upper surface: Yellow Group 6A. Lower surface: Yellow Group 8B.

General tonality: On open flower Yellow-Orange Group 18A with intonations of Orange Group 24B and 24C toward the center. No change in general tonality after the $10^{th}$ day. Afterwards, general tonality is Yellow-Orange Group 18B.

Petals:

*Petal reflex.*—Outer petals reflex somewhat.

*Margin.—Strong undulations of margin observed.*

*Shape.*—Generally broad elliptical in shape. Apex: Rounded. Base: Acute.

*Size.*—35 mm (l)×35 mm (w).

*Texture.*—Smooth.

*Thickness.*—Average.

*Arrangement.*—Not formal.

Petaloids:

*Quantity.*—23 on average.

*Shape.*—Narrow elliptical to somewhat irregular and asymmetric.

*Margins.*—Very strong undulations.

*Color.*—Upper surface: Greyed-Orange Group 167A with faint streaks of Yellow Group 7C. Basal petal spot Yellow Group 7C. Lower surface: Underlying base color is Yellow Group 8C with an overlay of Greyed-Orange Group 167A to Orange Group 24C. Intonations of Basal petal spot Yellow Group 8C.

*Size.*—15 to 23 m (l)×10 to 17 mm (w).

Reproductive organs:

*Pollen.*—Quantity: Scant. Color: Greyed-Orange Group 168A.

*Anthers.*—Size: 2.5 mm in length. Color: Yellow Group 8B with margins Greyed-Orange Group 168A. Quantity: Normally 90 to 100.

*Filaments.*—Color: Yellow Group 9A. Length: 6 mm.

*Pistils.*—Length: 7 to 8 mm. Quantity: Normally 70 to 75.

*Stigmas.*—Superior in location relative to the length of the filaments and the height of the anthers. Color: Greyed-Yellow Group 160A to Yellow Group 8A blend.

*Styles.*—Color: Red Group 50A.

*Hips.*—None Observed in the filed nursery in Jackson County Oreg.

PLANT

Plant growth: Upright to bushy. When grown as a budded field grown plant of *Rosa multiflora* understock the average height is 150 cm. Average spread is 100 cm.

Stems:

*Color.*—Juvenile growth: Yellow-Green Group 145C. Mature growth: Yellow-Green Group 146B.

*Length.*—On average, canes are 100 cm from the base of the plant to the flowering portion.

*Stem diameter.*—6 to 7 mm.

*Internodes.*—On mature canes, there is an average distance of 36 mm between nodes.

*Surface texture.*—Young wood: Somewhat rough. Older wood: Somewhat rough.

Thorns:

*Incidence.*—7 thorns per 10 cm of stem.

*Shape.*—Upper side: Flat. Lower side: Concave.

*Juvenile thorn color.*—Greyed-Red Group 181A.

*Mature thorn color.*—Greyed-Yellow Group 160A.

Plant foliage: Normally 7 leaflets found on compound leaves at mid stem.

*Compound leaf.*—110 m (l)×75 (w).

*Quantity.*—3 leaves per 10 cm of stem on average.

*Color of mature foliage.*—Upper side: Yellow-Green Group 147A. Lower side: Yellow-Green Group 147B.

*Color of juvenile foliage.*—Upper side: Green Group 137C with anthocyanic intonations of Greyed-Purple Group 183A. Lower side: Yellow-Green Group 146B with anthocyanic intonations of Greyed-Purple 183B to 183C.

Plant leaves and leaflets:

*Stipules.*—Size: 20 mm in length. Shape: Linear, slightly broad based with outward extending apecies. Margins: Finely serrated with many stipitate glands. Color: Yellow-Green Group 146A.

*Petiole.*—Length: 20 to 22 mm. Diameter: 2 mm.

*Upper surface.*—Color: Yellow-Green Group 145D to Greyed-Red Group 162D.

*Lower surface.*—Color: Yellow-Green Group 145A.

*Observations.*—Few stipitate glands. Few small prickles.

*Rachis.*—Length: 50 mm. Upper surface: Color: Yellow-Green Group 146B. Lower surface: Color: Yellow-Green Group 145A. Observations: Few stipitate glands. Few small prickles.

*Leaflet.*—Edge: Doubly serrated. Size: Average size of the terminal leaflet on normal leaves is 40 mm in length by 30 mm wide. Shape: Generally ovate. Base: Obtuse. Apex: Acuminate. Texture: Smooth. Thickness: Average. Arrangement: Odd pinnate. Ventation: Reticulate. Glossiness: Somewhat glossy.

Disease resistance: Above average resistance to powdery and downy mildews, rust, black spot, and *Botrytis* under normal growing conditions in Jackson County, Oreg.

Cold hardiness: The variety 'Poulfl003' has been found to be cold tolerant to USDA Cold Hardiness Zone 6.

What is claimed:

1. A new and distinct variety of rose plant of the floribunda rose class named 'Poulfl003', substantially as illustrated and described herein as a distinct and novel rose variety due to its abundant apricot flowers, dark green foliage, disease resistance, and extended period of bloom.

* * * * *

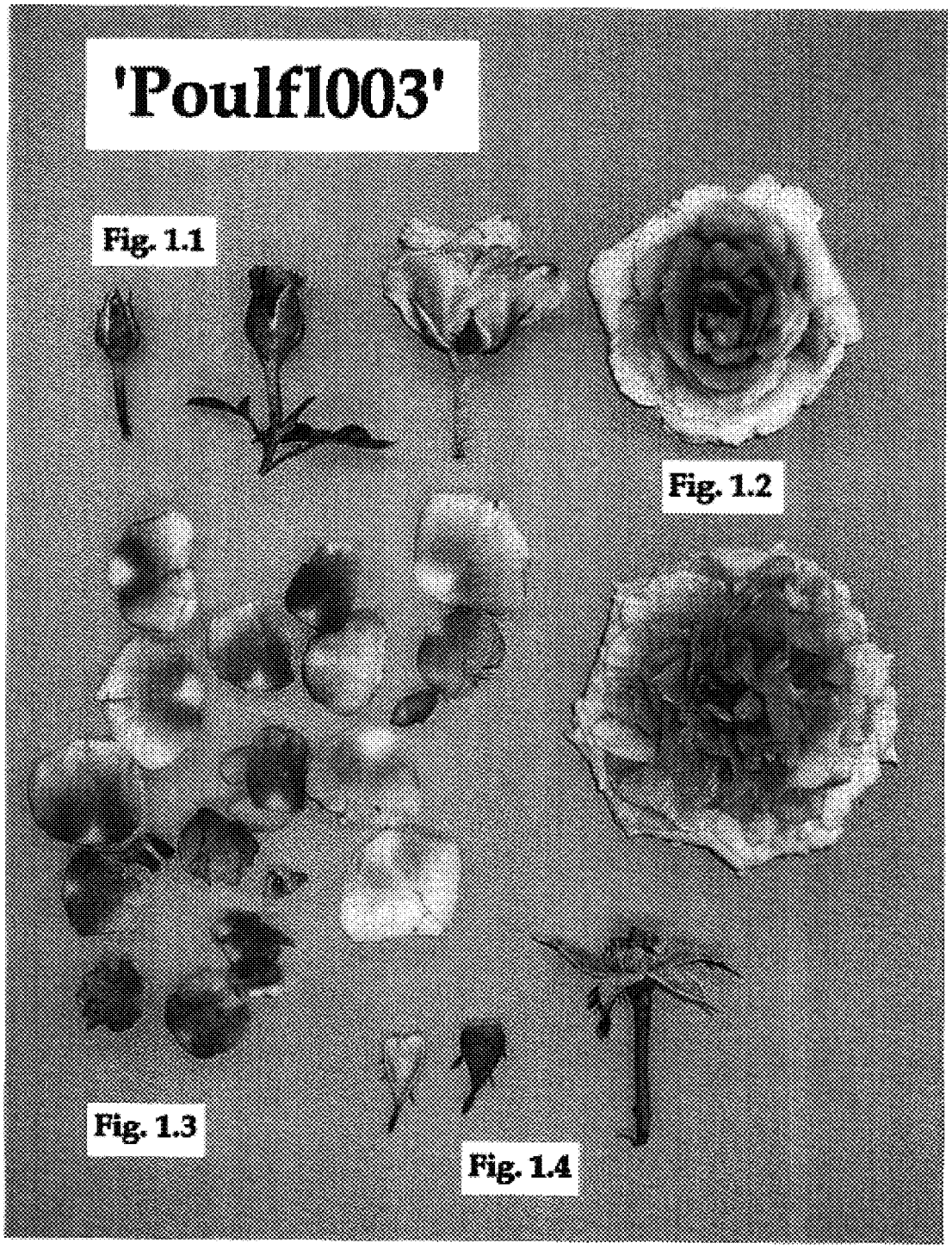
'Poulfl003'
Fig. 1.1
Fig. 1.2
Fig. 1.3
Fig. 1.4

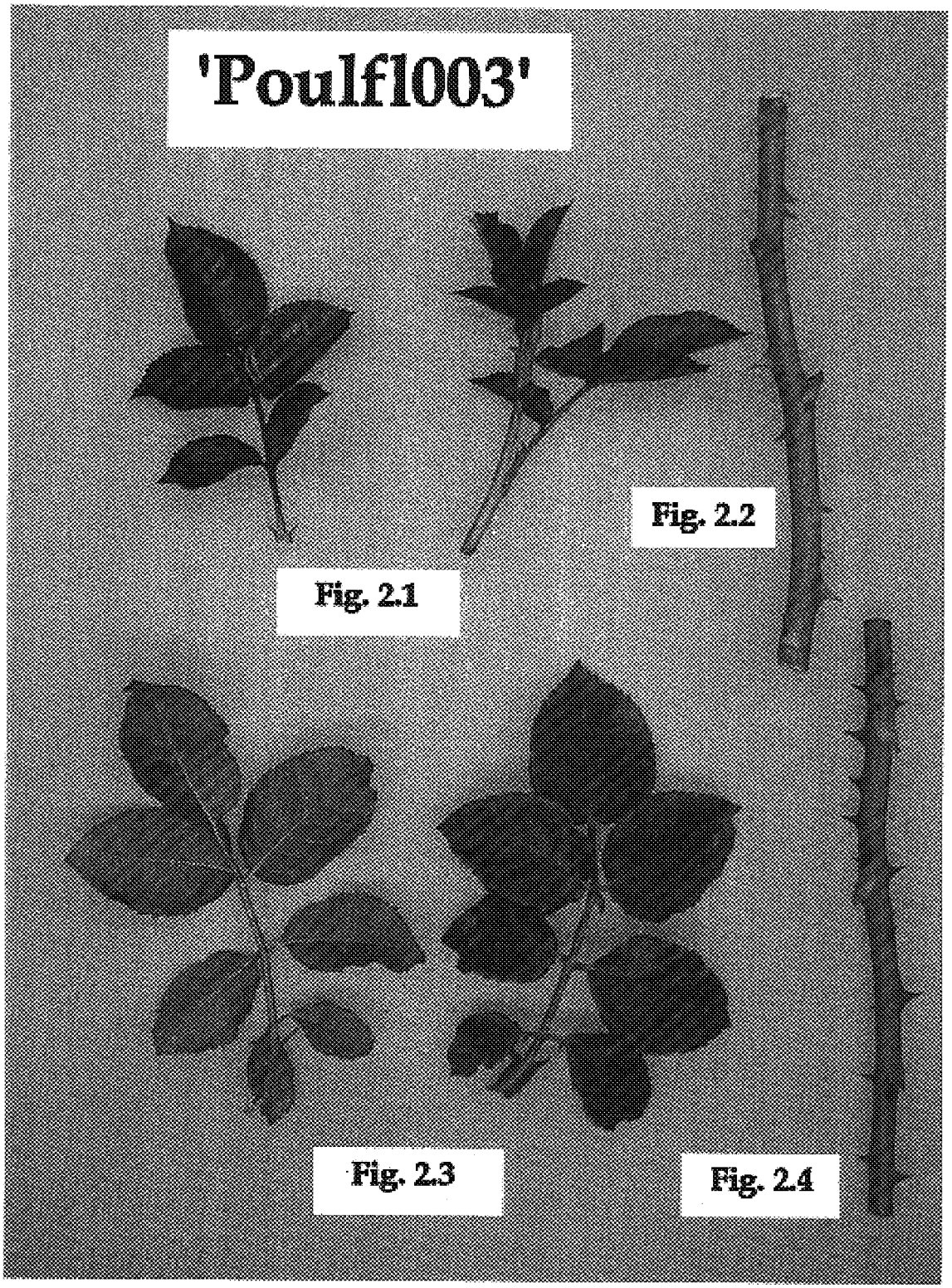
'Poulf1003'
Fig. 2.1
Fig. 2.2
Fig. 2.3
Fig. 2.4